US010386313B2

(12) United States Patent
Mazor et al.

(10) Patent No.: US 10,386,313 B2
(45) Date of Patent: Aug. 20, 2019

(54) CLOSED-LOOP CONTROL OF X-RAY KNIFE EDGE

(71) Applicant: BRUKER JV ISRAEL LTD., Migdal HaEmek (IL)

(72) Inventors: Isaac Mazor, Haifa (IL); Yuri Vinshtein, Hadera (IL); Matthew Wormington, Littleton, CO (US); Nikolai Kasper, Rheinzabern (DE)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 174 days.

(21) Appl. No.: 15/717,961

(22) Filed: Sep. 28, 2017

(65) Prior Publication Data

US 2018/0088062 A1 Mar. 29, 2018

Related U.S. Application Data

(60) Provisional application No. 62/401,183, filed on Sep. 29, 2016.

(51) Int. Cl.
*G01N 23/20091* (2018.01)
*G01S 17/48* (2006.01)
(Continued)

(52) U.S. Cl.
CPC ..... *G01N 23/20091* (2013.01); *G01N 23/201* (2013.01); *G01N 23/20008* (2013.01);
(Continued)

(58) Field of Classification Search
CPC ............ G01N 21/9501; G01N 21/211; G01N 21/95623; G01N 23/201; G01N 23/2008; G01B 11/0641; G21K 1/06
See application file for complete search history.

(56) References Cited

U.S. PATENT DOCUMENTS 4,675,892 A    6/1987   Plessis et al.
4,953,189 A    8/1990   Wang et al.
(Continued)

FOREIGN PATENT DOCUMENTS

| CN | 105960590 A | 9/2016 |
|---|---|---|
| CN | 104483337 B | 2/2017 |
| WO | 2008149372 A2 | 12/2008 |

OTHER PUBLICATIONS

TW Application # 106133498 search report dated Dec. 11, 2018.

*Primary Examiner* — Yara B Green
(74) *Attorney, Agent, or Firm* — Kligler & Associates

(57) ABSTRACT

Apparatus for X-ray scatterometry includes an X-ray source, which directs an X-ray beam to be incident at a grazing angle on an area of a surface of a sample, and an X-ray detector measures X-rays scattered from the area. A knife edge is arranged parallel to the surface of the sample in a location adjacent to the area so as to define a gap between the surface and the knife edge and to block a portion of the X-ray beam that does not pass through the gap. A motor moves the knife edge perpendicular to the surface so as to control a size of the gap. An optical rangefinder receives optical radiation reflected from the surface and outputs a signal indicative of a distance of the knife edge from the surface. Control circuitry drives the motor responsively to the signal in order to regulate the size of the gap.

16 Claims, 3 Drawing Sheets

(51) Int. Cl.
*G01N 23/201* (2018.01)
*G01S 17/88* (2006.01)
*G01N 23/20008* (2018.01)
*G01S 17/08* (2006.01)

(52) U.S. Cl.
CPC .............. *G01S 17/08* (2013.01); *G01S 17/48* (2013.01); *G01S 17/88* (2013.01); *G01N 2223/0563* (2013.01)

(56) References Cited

U.S. PATENT DOCUMENTS

| | | | |
|---|---|---|---|
| 5,101,226 A | 3/1992 | Beaulieu et al. | |
| 5,400,386 A | 3/1995 | Amemiya et al. | |
| 5,432,831 A | 7/1995 | Nagai et al. | |
| 6,512,814 B2* | 1/2003 | Yokhin | G01T 1/36 378/82 |
| 6,718,008 B1 | 4/2004 | He et al. | |
| 6,865,030 B2 | 3/2005 | Berto et al. | |
| 7,106,832 B2 | 9/2006 | Klunder et al. | |
| 7,113,566 B1* | 9/2006 | Peled | G01N 23/20 378/160 |
| 7,269,245 B2 | 9/2007 | He et al. | |
| 7,386,097 B2 | 6/2008 | Kerpershoek | |
| 7,406,153 B2* | 7/2008 | Berman | G01N 23/20 378/86 |
| 7,453,985 B2 | 11/2008 | Mazor et al. | |
| 7,551,719 B2 | 6/2009 | Yokhin et al. | |
| 7,977,258 B2 | 7/2011 | Nenyei et al. | |
| 8,243,878 B2 | 8/2012 | Yokhin et al. | |
| 8,687,766 B2* | 4/2014 | Wormington | G01N 23/207 378/70 |
| 8,731,138 B2 | 5/2014 | Yokhin et al. | |
| 2003/0123610 A1* | 7/2003 | Okanda | G01N 23/20 378/71 |
| 2004/0156474 A1* | 8/2004 | Yokhin | G01N 23/20 378/70 |
| 2006/0023837 A1* | 2/2006 | He | G01N 23/20 378/70 |
| 2012/0195406 A1 | 8/2012 | Asano et al. | |
| 2015/0247811 A1 | 9/2015 | Yun et al. | |

* cited by examiner

CLOSED-LOOP CONTROL OF X-RAY KNIFE EDGE

CROSS-REFERENCE TO RELATED APPLICATION

This application claims the benefit of U.S. Provisional Patent Application 62/401,183, filed Sep. 29, 2016, which is incorporated herein by reference.

FIELD OF THE INVENTION

The present invention relates generally to instruments for material and process analysis, and specifically to instruments and methods for analysis of thin layers and arrays of structures using X-rays.

BACKGROUND

In X-ray scatterometry measurements, a beam of X-rays is incident on a sample, and the intensity distribution of the X-rays scattered from the array of features is measured by a suitable detector. Some measurement modalities operate in a reflective geometry, in which an X-ray beam is incident on one side of the sample and is reflected (by specular and/or diffuse reflection) from the same side of the sample. Such reflection generally takes place only with X-ray beams incident at grazing angles, i.e., low angles of incidence, generally along a beam axis that is within 4° of the surface, and often below 1° from the surface.

Because of the low angle of incidence, the incident X-ray beam extends over an elongated area of the surface, referred to as the beam "footprint," and the scattering measurements have correspondingly low spatial resolution and require large measurement areas. To enhance the spatial resolution, some scatterometry systems use a knife edge, placed above the sample at the point at which the X-ray beam is incident on the surface. The knife edge is positioned so as to create a small gap between the blade and the surface of the sample through which the X-rays must pass in order reach the detector, thus reducing the effective length of the footprint. In the context of the present description and in the claims, the term "knife edge" refers to any type of straight edge (not necessarily very sharp) that is positioned near the surface of a sample in order to create a small gap between the knife edge and the surface and to block X-rays outside the gap.

An arrangement of this sort is described, for example, in U.S. Pat. No. 6,512,814, whose disclosure is incorporated herein by reference. This patent describes reflectometry apparatus, which includes a radiation source, adapted to irradiate a sample with radiation over a range of angles relative to a surface of the sample, and a detector assembly, positioned to receive the radiation specularly reflected from the sample over the range of angles and to generate a signal responsive thereto. A shutter is adjustably positionable to intercept the radiation. The shutter has a blocking position, in which it blocks the radiation in a lower portion of the range of angles, and a clear position, in which the radiation in the lower portion of the range reaches the array substantially without blockage. A dynamic knife edge is positioned over the surface. Preferably, the dynamic knife edge is operated in conjunction with the above-mentioned dynamic shutter. For measurements at low incidence angles, the knife edge is lowered very near to the surface, intercepting the incident X-ray beam and thus reducing the lateral dimension of the spot on the surface (i.e., the dimension in the direction along the surface that is roughly parallel to the beam axis).

U.S. Pat. No. 7,551,719, whose disclosure is incorporated herein by reference, describes another multifunction X-ray analysis system, which combines X-ray reflectometry (XRR) with small-angle X-ray scattering (SAXS) and X-ray diffraction (XRD) measurement. In one embodiment, shown in FIG. 5 of this patent, a knife edge is made of a cylindrical, X-ray absorbing material, such as a metal wire. This arrangement is said to permit the lower edge of the knife to be placed very close to the surface of the sample, on the order of 3 µm above the surface, without risk of damaging the sample. The wire can be aligned with the surface accurately and thus provides a small gap above the surface whose effective height is uniform over the entire angular range of interest, typically 0-4°.

U.S. Pat. No. 7,406,153, whose disclosure is incorporated herein by reference, describes apparatus for analysis of a sample that includes a radiation source, which is configured to direct a beam of radiation along a beam axis to impinge on a target area on a surface of the sample. A detector assembly is configured to sense the radiation scattered from the sample. A beam control assembly includes a beam blocker, which has a lower side adjoining the surface of the sample, and which contains front and rear slits perpendicular to the lower side that together define a beam plane that contains the beam axis and passes through the target area. In some embodiments, a beam limiter is positioned within the beam plain so as to block a portion of the plain. The beam limiter has a knife edge, which is transverse to the beam plane and typically protrudes below the lower side of the beam blocker.

SUMMARY

Embodiments of the present invention that are described hereinbelow provide methods and systems for X-ray analysis with enhanced beam control.

There is therefore provided, in accordance with an embodiment of the invention, apparatus for X-ray scatterometry, including an X-ray source, which is configured to generate and direct an X-ray beam to be incident at a grazing angle on an area of a surface of a sample. An X-ray detector is configured to measure X-rays scattered from the area in response to the incident X-ray beam. A knife edge is arranged parallel to the surface of the sample in a location adjacent to the area on which the X-ray beam is incident so as to define a gap between the surface and the knife edge and to block a portion of the X-ray beam that does not pass through the gap. A motor is configured to move the knife edge in a direction perpendicular to the surface of the sample so as to control a size of the gap. An optical rangefinder is configured to receive optical radiation reflected from the surface of the sample and to output a signal indicative of a distance of the knife edge from the surface of the sample responsively to the received optical radiation. Control circuitry is configured to drive the motor responsively to the signal output by the optical rangefinder in order to regulate the size of the gap.

In some embodiments, the X-ray detector is configured to measure an angular spectrum of the X-rays scattered from the area, and the apparatus includes a processor, which is configured to analyze the angular spectrum so as to assess a property of the sample.

In a disclosed embodiment, the knife edge includes a single crystal of a semiconductor or metal material. Alternatively, the knife edge may comprise a suitable polycrystalline or amorphous material. Additionally or alternatively, the motor includes a piezoelectric motor, which is configured to set the size of the gap with a resolution finer than 1 µm.

In some embodiments, the optical rangefinder is connected to move with the knife edge under control of the motor. In a disclosed embodiment, the optical rangefinder includes a laser, which is configured to direct an optical beam to impinge on the surface of the sample in proximity to the knife edge, and a detector, which is configured to sense the optical beam that is reflected from the surface. The detector may include a position-sensitive detector, which is arranged so that a position of the reflected optical beam on the detector varies with movement of the knife edge.

In a disclosed embodiment, the control circuitry is configured to drive the motor to set the size of the gap a target height responsively to an intensity of the scattered X-rays measured by the X-ray detector, which varies with the size of the gap, and thereafter to maintain the size of the gap at the target height responsively to the signal output by the optical rangefinder.

There is also provided, in accordance with an embodiment of the invention, a method for X-ray scatterometry, which includes directing an X-ray beam to be incident at a grazing angle on an area of a surface of a sample, and measuring X-rays scattered from the area in response to the incident X-ray beam. A knife edge is positioned parallel to the surface of the sample in a location adjacent to the area on which the X-ray beam is incident so as to define a gap between the surface and the knife edge and to block a portion of the X-ray beam that does not pass through the gap. An optical rangefinder receives optical radiation reflected from the surface of the sample and outputs a signal that is indicative of a distance of the knife edge from the surface of the sample responsively to the received optical radiation. The knife edge is moved in a direction perpendicular to the surface of the sample responsively to the signal output by the optical rangefinder so as to control a size of the gap.

The present invention will be more fully understood from the following detailed description of the embodiments thereof, taken together with the drawings in which:

DETAILED DESCRIPTION OF EMBODIMENTS

In reflectance-geometry X-ray scatterometry systems that are known in the art, the position of the knife edge is sometimes set by sensing the intensity of X-rays transmitted through the gap between the knife edge and the surface of the sample. Once the knife edge has been set in this manner to the desired height, it is locked in place during subsequent scatterometry measurements. In practice, when this approach is used, the knife edge cannot be placed any closer to the surface than about 10 µm. Furthermore, the gap between the knife edge and the surface may vary during the scatterometry measurement due to vibrations, for example. These limitations on knife edge positioning result in a large and possibly variable beam footprint, thus increasing the effective footprint and incident intensity fluctuations and degrading accuracy and precision of the scatterometry measurements.

Embodiments of the present invention that are described herein address these problems by using an optical rangefinder in regulating the size of the gap between the knife edge and the sample surface. The rangefinder receives optical radiation reflected from the surface of the sample and outputs signal indicative of the distance of the knife edge from the surface. (The term "optical radiation," as used in the present description and in the claims, refers to visible, infrared, or ultraviolet radiation, as opposed to the X-ray radiation that is used in the scatterometry measurements.) Control circuitry drives a motor in response to the signal output by the rangefinder in order to set and maintain the desired size of the gap, both before and during the scatterometry measurements. Using this sort of optical control, the gap between the knife edge and the sample surface can be set and held at sizes below 1 µm, with a resolution finer than 1 µm, which cannot be achieved by X-ray-based measurement techniques that are known in the art.

Figure 1:
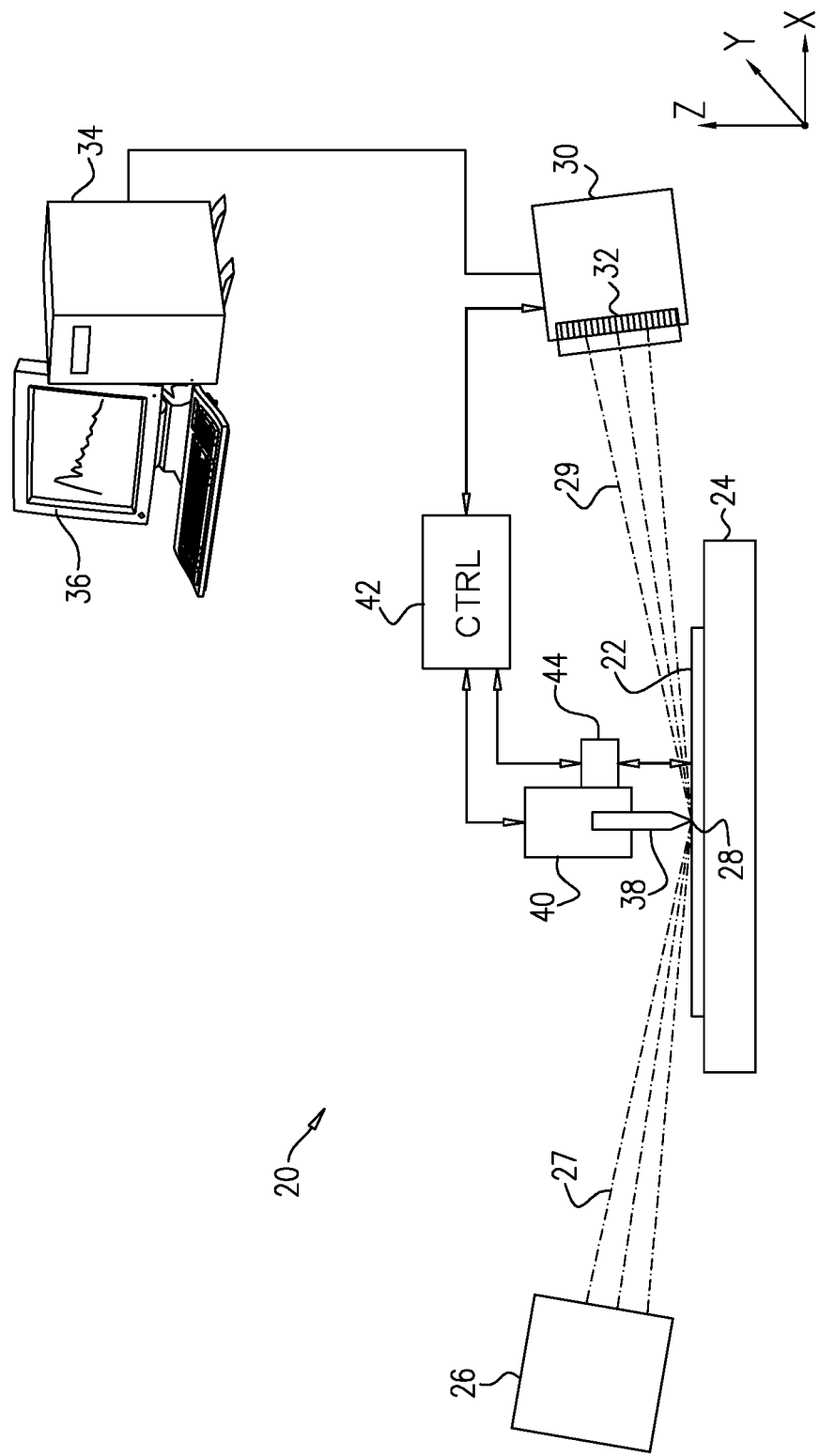
FIG. 1 is schematic side view of a system for X-ray scatterometry in reflection mode, in accordance with an embodiment of the invention.

FIG. 1 is a schematic illustration of a system 20 for X-ray scatterometry of a sample 22, in accordance with a preferred embodiment of the present invention. In the pictured embodiment, system 20 is configured for X-ray reflectometry. Alternatively, system 20 may be configured, mutatis mutandis, for other sorts of scatterometric measurements, including X-ray fluorescence (XRF), particularly grazing-incidence X-ray fluorescence (GIXRF), small-angle X-ray scattering (SAXS), grazing-incidence SAXS, and X-ray diffraction (XRD) measurements.

Sample 22, such as a semiconductor wafer, is mounted on a motion stage 24, allowing accurate adjustment of its position in three dimensions (X-Y-Z) and orientation. To reduce possible vibrations, stage 24 may be mounted, for example, on a massive base, with pads for vibration damping (not shown), as are known in the art.

An X-ray source 26, such as an X-ray tube with suitable monochromatizing optics (not shown), generates and directs an X-ray beam 27 to be incident at a grazing angle on a small area 28 on the surface of sample 22. Beam 27 may be collimated or focused onto area 28. A typical X-ray energy for this sort of reflectometric measurements in system 20 is about 8.05 keV (CuKα). Alternatively, other energies may be used, such as 5.4 keV (FeKα) or 4.5 keV (TiKα). These lower energies make it possible to work at a higher angle of incidence, and thus with a reduced footprint on the sample surface, but generally require that the system be housed in a vacuum chamber (not shown) to minimize attenuation and scattering of the X-rays by the ambient environment.

A reflected beam 29 of X-rays from sample 22 is collected by a detector assembly 30. Typically, assembly 30 collects reflected X-rays over a range of reflection angles between about 0° and 3°, both below and above the critical angle of the sample for total external reflection. In the pictured example, assembly 30 comprises an X-ray-sensitive detector array 32, although other sorts of detectors may alternatively be used. Detector array 32 measures the angular spectrum of the X-rays scattered from area 28. This spectrum represents the flux of X-ray photons scattered from sample 22 as a function of angle at a given energy or over a range of energies. For measurements of the dimensional parameters of a periodic structure on sample 22, such as pitch and feature widths (also known as critical dimensions), the scattered X-ray intensity distribution is typically measured as a function of angle in directions both perpendicular and parallel to the surface of the sample, for example using an area (2D) X-ray-sensitive detector.

A processor 34 analyzes the angular spectrum of the scattered X-rays so as to assess a property of sample 22, and outputs the results of the analysis to a display 36. In the case of XRR, the oscillatory structure of the angular spectrum perpendicular to the sample surface can be analyzed to determine the thickness, density and surface quality of one or more surface layers on sample 22. The spatial resolution and precision of these measurements, however, are limited by the size of the elongated footprint of beam 27 on area 28 of the sample surface.

As another example, in the case of grazing-incidence SAXS measurements, the X-ray intensity scattered parallel to the sample surface can be analyzed to determine geometrical parameters of an array of scattering structures on the surface, including the in-plane spacing of the structures, widths at different heights and roughness. The intensity scattered from a periodic array of this sort, with sub-micron in-plane spacing between adjacent structures, is substantially concentrated in a series "rods," with angular spacing inversely proportional to the pitch of the array.

To reduce the size of the footprint, a knife edge 38 is arranged parallel to the surface of sample 22 in a location adjacent to area 28 on which X-ray beam 27 is incident. As explained above, knife edge 38 defines a gap between the surface of sample 22 and the knife edge and blocks the portion of X-ray beam 27 that does not pass through the gap. The geometry (width, height and shape) of the knife edge are optimized so as not to touch the sample surface at small gap heights, even with curved samples. Knife edge 38 may comprise any suitable sort of X-ray absorbing material, such as a metal blade or wire or, alternatively, a single crystal of a semiconductor material (such as Si, Ge or InP) or metal (such as Ta or W). These latter sorts of single crystals are advantageous in that they scatter X-rays (by diffraction) in certain well-defined directions. Knife edge 38 can then be oriented so that X-rays will not scatter off the knife edge itself toward detector array 32. Optionally, other beam-limiting elements, such as a shutter and/or a vertical slit, may be used in conjunction with knife edge 38, as described, for example, in the patents cited above.

A motor 40 moves knife edge 38 in a direction perpendicular to the surface of sample 22 so as to control the size of the gap. A control circuit 42, such as a proportional-integral-derivative (PID) controller, drives the motor in response to inputs from other elements of system 20. In one embodiment, motor 40 comprises a piezoelectric motor, which is able to set the size of the gap with a resolution finer than 1 µm and reliably reach gap sizes smaller than 1 µm. Alternatively, other sorts of precision motors, as are known in the art, may be used in positioning knife edge 38. (The term "motor" is used in the context of the present description and in the claims to denote any device that converts electrical energy into mechanical motion.)

Figure 2:
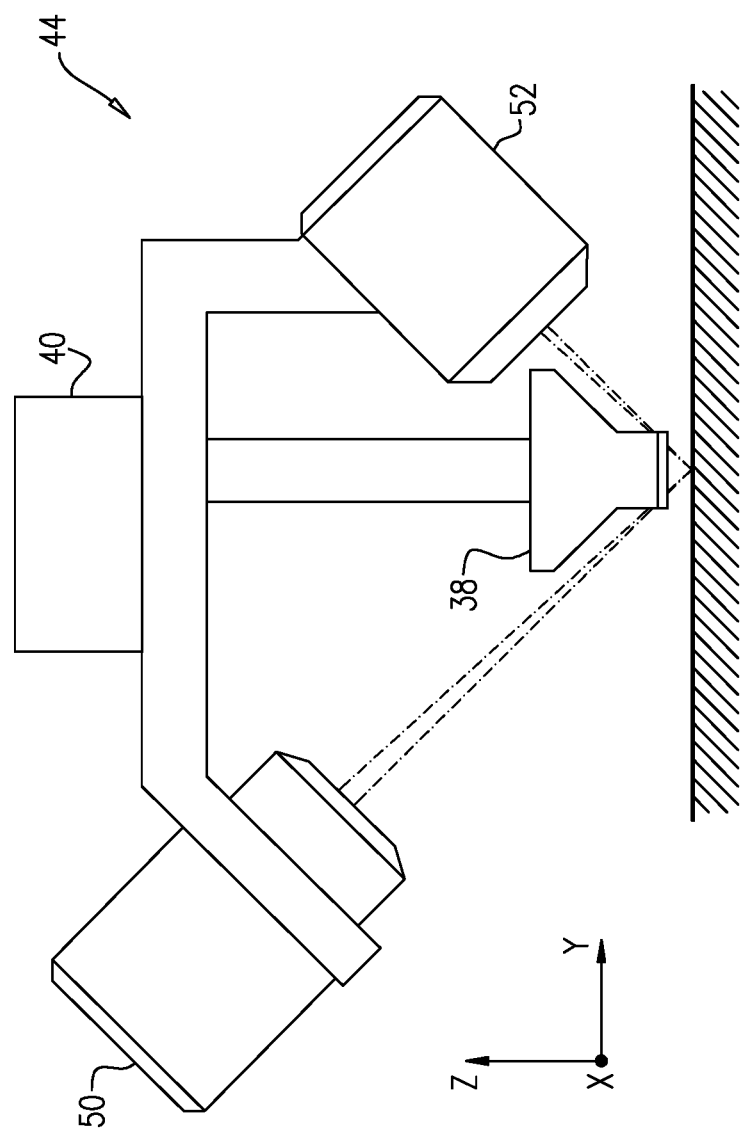
FIG. 2 is a schematic side view of a knife edge with optical control, in accordance with an embodiment of the invention.

Control circuit 42 drives motor 40 based on a feedback signal, indicative of the distance of knife edge 38 from the surface of sample 22, that is output by an optical rangefinder 44 based on optical radiation reflected from the surface of sample. Details of a particular type and configuration of optical rangefinder that can be used for this purpose are shown in FIG. 2 and described with reference thereto hereinbelow. Alternatively, other sorts of optical distance-measurement devices, including both commercially-available and purpose-built instruments, can be used as rangefinders for this purpose and are considered to be within the scope of the present invention.

FIG. 2 is a schematic side view of knife edge 38 and optical rangefinder 44, in accordance with an embodiment of the invention. The view in this figure is rotated by 90° about the Z-axis relative to FIG. 1. In this embodiment, optical rangefinder 44 is placed at right angles to the X-ray beam. In other embodiments, however, the optical rangefinder may be rotated to other orientations. In the pictured embodiment, optical rangefinder 44 is connected to move with knife edge 38 under control of motor 40, with a connection that is sufficiently rigid to ensure that the spatial relations between elements of the rangefinder and the knife edge remain fixed to within the positioning tolerance of the knife edge.

Optical rangefinder 44 comprises a laser 50, which directs an optical beam to impinge on the surface of sample 22 in proximity to knife edge 38. A detector 52 senses the optical beam that is reflected from the surface and outputs a signal to control circuit 42 that indicates the height of knife edge 38 above the sample surface. In the present example, detector 52 comprises a position-sensitive detector. As shown in the figure, laser 50 and detector 52 are arranged so that the laser beam strikes the sample surface at an angle. Thus, the position of the reflected optical beam on detector 52 will vary with vertical movement of knife edge 38 relative to the sample surface (or vice versa), in proportion to the height of the knife edge above the surface. Control circuit 42 uses the position variation signal output by detector as a feedback signal for control of motor 40.

Figure 3:
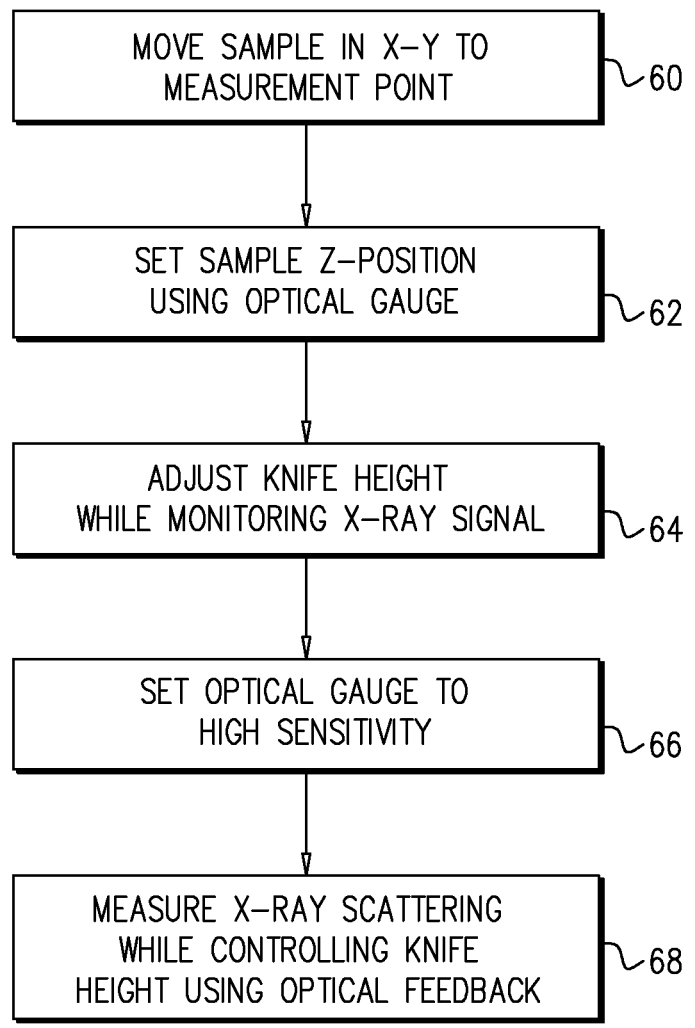
FIG. 3 is a flow chart that schematically illustrates a method for X-ray scattering measurement, in accordance with an embodiment of the invention.

FIG. 3 is a flow chart that schematically illustrates a method for X-ray scattering measurement, in accordance with an embodiment of the invention. The method is described, for the sake of clarity and concreteness, with reference to the specific elements of system 20 and rangefinder 44 that are shown in the preceding figures and described above. Alternatively, the principles of this method may be implemented, mutatis mutandis, in other X-ray scatterometry systems in which an optical rangefinder can be used in controlling the location of a knife edge.

To initiate the measurement, stage 24 moves sample 22 transversely (in the X-Y plane as shown in FIG. 1) so that the desired measurement point on the sample is located in area 28, where X-ray beam 27 will be incident, at a sample motion step 60. Once sample 22 is in the desired X-Y location, stage 24 adjusts the vertical (Z) position of the sample to coincide with the height of X-ray beam 27, at a sample height adjustment step 62. Optical rangefinder 44 can be used at this stage to verify that the sample height is approximately correct. Depending on the precision of adjustment afforded by stage 24, the maximum deviation of sample height relative to beam 27 can be adjusted in this step to within about 5 µm of the beam center.

Control circuit 42 now drives motor 40 to set the size of the gap between knife edge 38 and the surface of sample 22 to a selected target height, at a knife height adjustment step 64. For this purpose, X-ray source 26 is actuated, and control circuit 42 receives a reading of the intensity of the X-rays scattered from sample 22 that is measured by X-ray detector assembly 30. The measured intensity varies proportionally with the size of the gap, up to the diameter of X-ray beam 27, and thus provides an accurate measure of the gap size irrespective of the composition of the sample. Given sufficient precision in control of the height of knife edge 38 and in measurement of the scattered X-ray intensity, the gap size between the sample and knife edge 38 can be set in this step to within 0.3 µm of the target height.

The signal output by optical rangefinder 44 will now be used by control circuit 42 in maintaining the size of the gap precisely at the target height. For this purpose, rangefinder 44 can be set to operate at high sensitivity, with reduced range and increased resolution, at a sensitivity setting step 66.

System 20 now enters its measurement mode, in which processor 34 acquires the X-ray scattering spectrum of sample 22, at a scattering measurement step 68. Control circuit 42 uses the feedback signal from optical rangefinder 44 in precisely maintaining the gap size, by monitoring height changes and adjusting motor 40 accordingly. The bandwidth of the feedback control loop can be set, for example, to the range of 5-10 Hz in order to compensate for mechanical and thermal drift in system 20 during long measurements. As noted earlier, stage 24 can be mounted on a massive vibration-isolation and damping system, while the knife assembly is mounted on a mechanically rigid frame in order to minimize high-frequency vibrations above the response time of the feedback control loop. The use of real-time feedback from optical rangefinder 44 thus enables system 20 to measure X-ray scattering properties of sample 22 with finer spatial resolution and greater precision than were previously achievable.

Although the embodiments described above use optical sensing of the distance between the knife edge and the sample surface, other gauges capable of precisely measuring sub-micron displacement of the sample surface during X-ray measurements may alternatively be used. For example, a capacitance gauge or atomic force microscope (AFM) probe could be used in place of the optical rangefinder.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for X-ray scatterometry, comprising:
    an X-ray source, which is configured to generate and direct an X-ray beam to be incident at a grazing angle on an area of a surface of a sample;
    an X-ray detector, which is configured to measure X-rays scattered from the area in response to the incident X-ray beam;
    a knife edge, which is arranged parallel to the surface of the sample in a location adjacent to the area on which the X-ray beam is incident so as to define a gap between the surface and the knife edge and to block a portion of the X-ray beam that does not pass through the gap;
    a motor, which is configured to move the knife edge in a direction perpendicular to the surface of the sample so as to control a size of the gap;
    an optical rangefinder, which is configured to receive optical radiation reflected from the surface of the sample and to output a signal indicative of a distance of the knife edge from the surface of the sample responsively to the received optical radiation; and
    control circuitry, which is configured to drive the motor responsively to the signal output by the optical rangefinder in order to regulate the size of the gap.

2. The apparatus according to claim 1, wherein the X-ray detector is configured to measure an angular spectrum of the X-rays scattered from the area, and comprising a processor, which is configured to analyze the angular spectrum so as to assess a property of the sample.

3. The apparatus according to claim 1, wherein the knife edge comprises a single crystal of a semiconductor or metal material.

4. The apparatus according to claim 1, wherein the motor comprises a piezoelectric motor, which is configured to set the size of the gap with a resolution finer than 1 µm.

5. The apparatus according to claim 1, wherein the optical rangefinder is connected to move with the knife edge under control of the motor.

6. The apparatus according to claim 5, wherein the optical rangefinder comprises a laser, which is configured to direct an optical beam to impinge on the surface of the sample in proximity to the knife edge, and a detector, which is configured to sense the optical beam that is reflected from the surface.

7. The apparatus according to claim 6, wherein the detector comprises a position-sensitive detector, which is arranged so that a position of the reflected optical beam on the detector varies with movement of the knife edge.

8. The apparatus according to claim 1, wherein the control circuitry is configured to drive the motor to set the size of the gap to a target height responsively to an intensity of the scattered X-rays measured by the X-ray detector, which varies with the size of the gap, and thereafter to maintain the size of the gap at the target height responsively to the signal output by the optical rangefinder.

9. A method for X-ray scatterometry, comprising:
    directing an X-ray beam to be incident at a grazing angle on an area of a surface of a sample;
    measuring X-rays scattered from the area in response to the incident X-ray beam;
    positioning a knife edge parallel to the surface of the sample in a location adjacent to the area on which the X-ray beam is incident so as to define a gap between the surface and the knife edge and to block a portion of the X-ray beam that does not pass through the gap;
    receiving in an optical rangefinder optical radiation reflected from the surface of the sample and outputting a signal from the optical rangefinder that is indicative of a distance of the knife edge from the surface of the sample responsively to the received optical radiation; and
    moving the knife edge in a direction perpendicular to the surface of the sample responsively to the signal output by the optical rangefinder so as to control a size of the gap.

10. The method according to claim 9, wherein measuring the X-rays comprises acquiring an angular spectrum of the X-rays scattered from the area, and analyzing the angular spectrum so as to assess a property of the sample.

11. The method according to claim 9, wherein the knife edge comprises a single crystal of a semiconductor or metal material.

12. The method according to claim 9, wherein moving the knife edge comprises setting the size of the gap with a resolution finer than 1 µm.

13. The method according to claim 9, wherein the optical rangefinder is connected to move together with the knife edge under control of a motor.

14. The method according to claim 13, wherein the optical rangefinder comprises a laser, which is configured to direct an optical beam to impinge on the surface of the sample in proximity to the knife edge, and a detector, which is configured to sense the optical beam that is reflected from the surface.

15. The method according to claim 14, wherein the detector comprises a position-sensitive detector, which is arranged so that a position of the reflected optical beam on the detector varies with movement of the knife edge.

16. The method according to claim 9, wherein positioning the knife edge comprises setting the size of the gap to a target height responsively to a measurement of an intensity of the scattered X-rays, which varies with the size of the gap, and wherein moving the knife edge comprises maintaining the size of the gap at the target height responsively to the signal output by the optical rangefinder.

* * * * *